(12) United States Patent
Andersen et al.

(10) Patent No.: US 6,207,682 B1
(45) Date of Patent: Mar. 27, 2001

(54) MODIFIED RELEASE FORMULATIONS CONTAINING (R)-1-(10,11-DIHYDRO-5H-DIBENZO[A,D]CYCLOHEPTEN-5-YLIDENE)-1PROPYL)-3-PIPERIDINECARBOXYLIC ACID

(75) Inventors: Tina Meinertz Andersen, Hørsholm; Thyge Borup Hjorth, Farum; Kim Westi Jorgensen, Søborg, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/469,135

(22) Filed: Dec. 21, 1999

Related U.S. Application Data

(60) Provisional application No. 60/115,535, filed on Jan. 12, 1999.

(30) Foreign Application Priority Data

Dec. 22, 1998 (DK) .................................... PA 1998 01 703

(51) Int. Cl.[7] ................................................. A61K 31/445
(52) U.S. Cl. .......................................................... 514/317
(58) Field of Search ............................................... 514/317

(56) References Cited

U.S. PATENT DOCUMENTS 5,783,212  7/1998  Fassihi et al. .

FOREIGN PATENT DOCUMENTS

| 2 152 940 | 8/1985 | (GB) . |
| WO 95/18793 | 7/1995 | (WO) . |
| WO 97/22338 | 6/1997 | (WO) . |

OTHER PUBLICATIONS

Yang et al., Internation Journal of Pharmaceutics, vol. 155, pp. 219–229 (1997).

*Primary Examiner*—Raymond Henley, III
(74) *Attorney, Agent, or Firm*—Steve T. Zelson, Esq.; Carol E. Rozek, Esq.

(57) ABSTRACT

Modified release formulations with zero-order drug release containing (R)-1-(3-(10,11-Dihydro-5H-dibenzo[a,d]cyclohepten-5-ylidene)-1-propyl)-3-piperidinecarboxylic acid, or a pharmaceutically acceptable salt thereof, dispersed in a polymeric matrix having at least one release rate controlling polymer are useful in treating disorders related to both neurogenic inflammation and non-insulin-dependent diabetes mellitus (NIDDM).

10 Claims, 7 Drawing Sheets

MODIFIED RELEASE FORMULATIONS CONTAINING (R)-1-(10,11-DIHYDRO-5H-DIBENZO[A,D]CYCLOHEPTEN-5-YLIDENE)-1PROPYL)-3-PIPERIDINECARBOXYLIC ACID

CROSS-REFERENCES TO RELATED APPLICATIONS

This application claims priority under 35 U.S.C. 119 of U.S. provisional application no. 60/115,535 filed Jan. 12,1999 and of Danish application no. PA 1998 01703 filed Dec. 22,1998, the contents of which are fully incorporated herein by reference.

BACKGROUND OF THE INVENTION

1. Field of the Invention

The present invention relates to a novel formulation containing (R)-1-(3-(10,11-Dihydro-5H-dibenzo[a,d]cyclohepten-5-ylidene)-1-propyl)-3-piperidinecarboxylic acid or a pharmaceutically acceptable salt thereof, and to its use in the treatment and/or prophylaxis of certain disorders.

2. Description of the Related Art

WO 95/18793 and WO 97/22338 discloses inter alia (R)-1-(3-(10,11-Dihydro-5H-dibenzo[a,d]cyclohepten-5-ylidene)-1-propyl)-3-piperidinecarboxylic acid or a pharmaceutically acceptable salt thereof, and the use of the compound to treat all painful, hyperalgesic and/or inflammatory conditions in which C-fibres play a pathophysiological role by eliciting neurogenic pain or inflammation. Further, it has been demonstrated that (R)-1-(3-(10,11 -Dihydro-5H-dibenzo[a,d]cyclohepten-5-ylidene)-1-propyl)-3-piperidinecarboxylic acid or a pharmaceutically acceptable salt thereof, is useful in reducing blood glucose and/or inhibiting the secretion, circulation or effect of insulin antagonizing peptides like CGRP or amylin.

The formulations containing (R)-1-(3-(10,11 -Dihydro-5H-dibenzo[a,d]cyclohepten-5-ylidene)-1-propyl)-3-piperidinecarboxylic acid or a pharmaceutically acceptable salt thereof, as suggested in WO 95/18793 and WO 97/22338, relate to formulations which are prepared by conventional techniques. The formulations mentioned appear in conventional forms, for example capsules, tablets, aerosols, solutions, suspensions or topical applications.

The half-life for (R)-1-(3-(10,11-Dihydro-5H-dibenzo[a,d]cyclohepten-5-ylidene)-1-propyl)-3-piperidinecarboxylic acid is relatively short, and in order to control the release of the compound in such a manner that an effective concentration in the blood can be maintained over an extended period of time but also that the drug concentration in the blood remains relatively constant over an extended period of time, there exists a need for a modified release formulation for (R)-1-(3-(10,11-Dihydro-5H-dibenzo[a,d]cyclohepten-5-ylidene)-1-propyl)-3-piperidinecarboxylic acid.

The use of modified release formulations will furthermore improve patient compliance as it reduces the numbers of dosages to be taken per day.

Thus one object of the present invention is to provide modified release formulations containing (R)-1-(3-(10,11-Dihydro-5H-dibenzo[a,d]cyclohepten-5-ylidene)-1-propyl)-3-piperidinecarboxylic acid or a pharmaceutically acceptable salt thereof to reduce the fluctuations in plasma concentrations and thereby reduce any inconvenience therefrom.

To reduce plasma fluctuations it is necessary to provide modified release formulations with zero-order drug release. However, zero-order drug release is difficult to obtain for modified release products, especially for matrix tablets comprising hydroxypropylmethylcellulose, which is a polymer often used within modified release formulations.

SUMMARY OF THE INVENTION

It has now surprisingly been found that modified release formulations with zero-order drug release containing (R)-1-(3-(10,11-Dihydro-5H-dibenzo[a,d]cyclohepten-5-ylidene)-1-propyl)-3-piperidinecarboxylic acid or a pharmaceutically acceptable salt thereof dispersed in a polymeric matrix comprising at least one release rate controlling polymer can be provided.

The present invention further provides modified release formulations with zero-order drug release wherein the polymeric matrix comprises a combination of a polyethylene oxide and a hydroxypropylmethylcellulose so that the in vitro dissolution rate is decreased compared to what is obtained with polyethylene oxide alone as the rate controlling polymer.

Furthermore, the present invention relates to modified release formulations comprising a combination of a polyethylene oxide and a hydroxypropylmethylcellulose making the in vitro zero-order dissolution profile independent of pH, indicating that the in vivo absorption also is zero-order and independent of pH.

The requirements of the dissolution profile for the formulation depends on the disorders to be treated and thereby by the ratio between the polymers used. For disorders having a relatively short treatment period, for example during the night, the dissolution rate should be higher than for disorders requiring once daily treatment. The in vitro dissolution profiles can be modified according to the actual requirement.

The present invention further provides a method of treating conditions or indications related to all painful, hyperalgesic and/or inflammatory conditions in which C-fibres play a pathophysiological role, e.g. neurogenic pain, neurogenic inflammation, migraine, neuropathy, itching and rheumatoid arthritis; urinary incontinence; angiogenesis as well as indications caused by or related to the secretion and circulation of insulin antagonizing peptides, e.g. non-insulin-dependent diabetes mellitus (NIDDM) and ageing-associated obesity, by administering an effective and/or a prophylactic amount of a modified release formulation containing (R)-1-(3-(10,11-Dihydro-5H-dibenzo[a,d]cyclohepten-5-ylidene)-1-propyl)-3-piperidinecarboxylic acid or a pharmaceutically compound thereof to a patient in need thereof.

Furthermore, the present invention also provides the use of a modified release formulation containing (R)-1-(3-(10,11-Dihydro-5H-dibenzo[a,d]cyclohepten-5-ylidene)-1-propyl)-3-piperidinecarboxylic acid or a pharmaceutically compound thereof in the manufacture of a medicament, for treating the above mentioned conditions or indications.

The present invention also provides a pharmaceutical composition for use in the treatment of the above mentioned conditions or indications which comprises a modified release formulation containing (R)-1-(3-(10,11-Dihydro-5H-dibenzo[a,d]cyclohepten-5-ylidene)-1-propyl)-3-piperidinecarboxylic acid or a pharmaceutically compound thereof.

DETAILED DESCRIPTION OF THE INVENTION

Figure 1A:
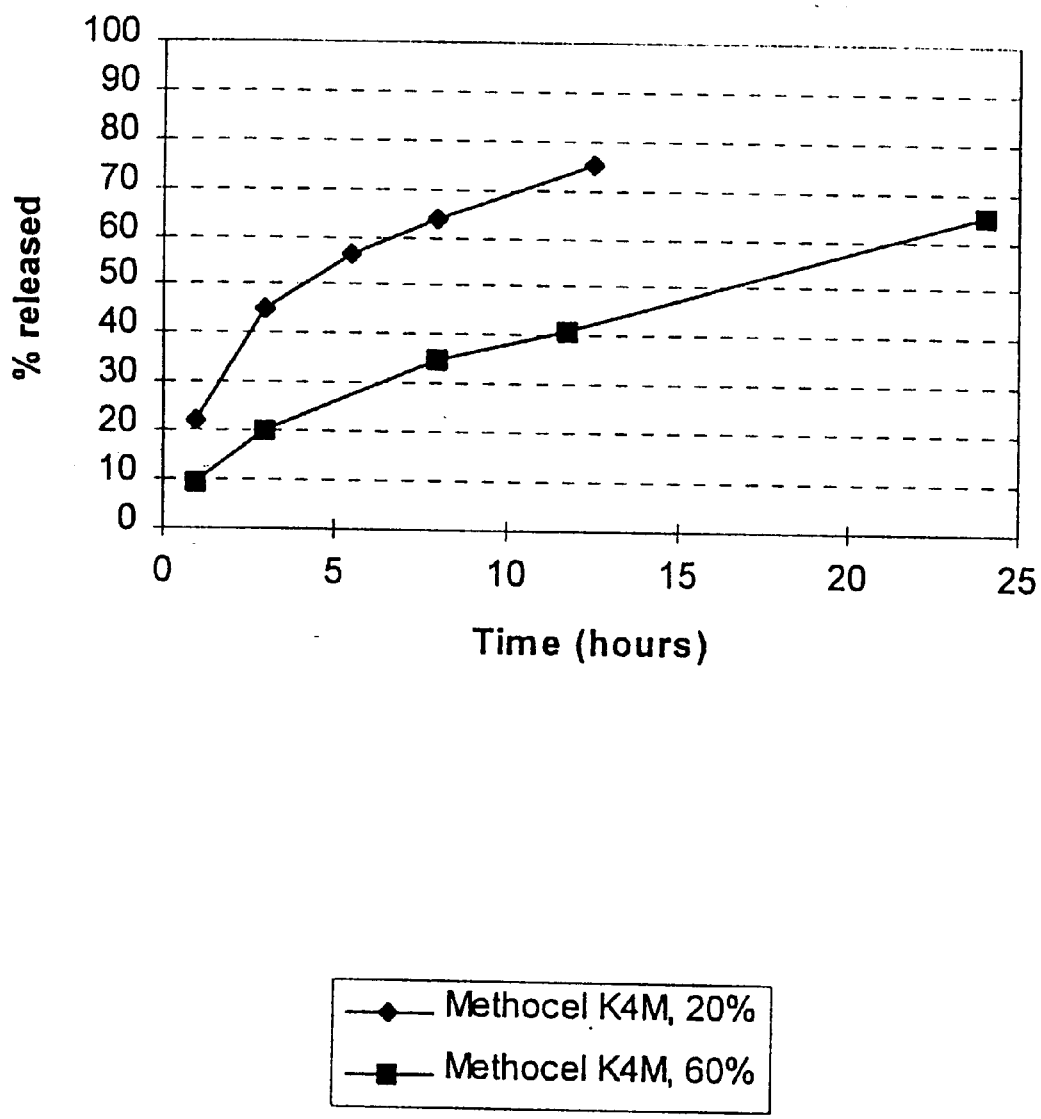
FIGS. 1a, 1b and 1c are graphs depicting in-vitro dissolution profiles for the tablet formulations shown in Example 1.

Accordingly, the present invention relates to a modified release formulation with zero-order drug release containing (R)-1-(3-(10,11-Dihydro-5H-dibenzo[a,d]cyclohepten-5-ylidene)-1-propyl)-3-piperidinecarboxylic acid or a pharmaceutically acceptable salt thereof dispersed in a polymeric matrix comprising at least one release rate controlling polymer.

Within the present invention (R)-1-(3-(10,11-Dihydro-5H-dibenzo[a,d]cyclohepten-5-ylidene)-1-propyl)-3-piperidinecarboxylic acid may optionally exist as a pharmaceutically acceptable acid addition salt, metal salt or, optionally alkylated, ammonium salt.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts. Further examples of pharmaceutically acceptable inorganic or organic acid addition salts include the pharmaceutically acceptable salts listed in *Journal of Pharmaceutical Science*, 66, 2 (1977) which are known to the skilled artisan.

Also included are the hydrates of the above mentioned acid addition salt which the present compound is able to form.

(R)-1-(3-(10,11-Dihydro-5H-dibenzo[a,d]cyclohepten-5-ylidene)-1-propyl)-3-piperidinecarboxylic acid may be administered in a pharmaceutically acceptable acid addition salt form or where possible as a metal or a lower alkylammonium salt. Such salt forms exhibit approximately the same order of activity as the free base forms.

In a preferred embodiment of the invention (R)-1-(3-(10,11-Dihydro-5H-dibenzo[a,d]cyclohepten-5-ylidene)-1-propyl)-3-piperidinecarboxylic acid is in the form of the hydrochloride salt.

(R)-1-(3-(10,11-Dihydro-5H-dibenzo[a,d]cyclohepten-5-ylidene)-1-propyl)-3-piperidinecarboxylic acid or a pharmaceutically acceptable salt thereof may be prepared according to the procedures generally outlined in WO 95/18793 and WO 97/22338.

By modified release is meant any formulation having prolonged, extended or delayed release.

Examples of modified release formulations which are suitable for incorporating (R)-1-(3-(10,11-Dihydro-5H-dibenzo[a,d]cyclohepten-5-ylidene)-1-propyl)-3-piperidinecarboxylic acid are described in Hui, H. W., Robinson, J. R. and Lee, V. H. L., Design and Fabrication of Oral Controlled Release Drug Delivery Systems, Controlled Drug Delivery, Fundamentals and Applications, Sec. Ed. edited by J. R. Robinson and V. H. L. Lee 373–432 1987.

The term "release rate controlling polymer" as used herein includes hydrophilic polymers, hydrophobic polymers or mixtures of hydrophilic and/or hydrophobic polymers that are capable of retarding the release of (R)-1-(3-(10,11-Dihydro-5H-dibenzo[a,d]cyclohepten-5-ylidene)-1-propyl)-3-piperidinecarboxylic acid in vivo when the compound is dispersed in a polymeric matrix formed from the release rate controlling polymers.

Examples of release rate controlling polymers to be used in this invention include hydroxyalkylcellulose, such as hydroxypropylmethylcellulose and hydroxypropylcellulose; polyethylene oxide; alkylcellulose such as ethylcellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; polyalkyl methacrylate; and polyvinyl acetate. Other suitable hydrophobic polymers include polymers or copolymers derived from acrylic or methacrylic acid esters, copolymers of acrylic and methacrylic acid esters, zein, waxes, shellac and hydrogenated vegetable oils.

In a preferred embodiment of the invention, the release rate controlling polymers include a hydroxypropylmethylcellulose, a polyethylene oxide, or a combination thereof.

In a particular embodiment of the invention there is provided a release formulation containing a polyethylene oxide.

In another particular embodiment of the invention there is provided a release formulation containing a hydroxypropylmethylcellulose and a polyethylene oxide.

An especially preferred type of hydroxypropylmethylcellulose for use in accordance with the invention is a hydroxypropylmethylcellulose sold under the trademark METHOCEL (Dow Chemical Co.) or equivalents. Suitable METHOCELS include the K grades such as METHOCEL K15M Premium CR, METHOCEL K100M Premium CR, METHOCEL K100 Premium LV and METHOCEL K4M Premium. Other suitable METHOCELS include the E, F and J grades.

An especially preferred type of polyethylene oxide for use in accordance with the invention is a polyethylene oxide sold under the trademark SENTRY POLYOX (Union Carbide Corp.) or equivalents. Suitable POLYOX's include the POLYOX WSR grades such as POLYOX WSR Coagulant, POLYOX WSR-301, POLYOX WSR-303, and POLYOX WSR-1105.

The hydroxypropylmethylcelluloses used according to the invention preferably have a viscosity (2 wt% solution at 20° C.) of about 100 to 100,000 cps. Especially suitable are METHOCEL K types or their equivalents. The polyethylene oxide used according to the invention preferably has a molecular weight of about 100,000 to 7,000,000, more preferably 900,000 to 7,000,000.

To ensure correct release kinetics, the formulation of the present invention contains about 5 and 75% by weight, preferably about 20 and 50% by weight, of release rate controlling polymer(s).

The modified release formulations according to the present invention may preferably include any relevant filler. The choice of these excipients and their quantity may easily be determined by a person skilled in the art. The exicipients include diluents, various binders, disintegrants, lubricants, colorants, sweeteners and the like.

Suitable diluents include pharmaceutically acceptable inert fillers such as microcrystalline cellulose, lactose, dibasic calcium phosphate, saccharides, and/or mixtures of any of the foregoing. Examples of diluents include microcrystalline cellulose such as AVICEL pH112, AVICEL pH101 and AVICEL pH102; lactose such as lactose monohydrate, lactose anhydrous, and PHARMATOSE DCL 21, dibasic calcium phosphate such as EMCOMPRESS, mannitol, starch, sorbitol, sucrose and glucose.

Suitable lubricants include, for example, colloidal silicon dioxide such as AEROSIL 200, talc, stearic acid, magnesium stearate and calcium stearate.

Suitable binders include polyethylene glycols such as PEG 6000, cetostearyl alcohol, cetyl alcohol, polyoxyethylene alkyl ethers, polyoxyethylene castor oil derivatives, polyoxyethylene sorbitan fatty acid esters, polyoxyethylene stearates, polyoxamers and waxes.

The modified release formulation can be produced either by using a granulation method followed by compression or by direct compression, thereby avoiding the granulation process step.

Preferred formulations of the modified release formulations are ultimately enteric coated tablets or capsules, wax or polymer coated tablets or capsules or time-release matrices, or combinations thereof. Particular preferred formulations are matrix tablets.

(R)-1-(3-(10,11-Dihydro-5H-dibenzo[a,d]cyclohepten-5-ylidene)-1-propyl)-3-piperidinecarboxylic acid or a pharmaceutically acceptable salt thereof in the form of a modified release formulation can be used in the treatment of conditions or indications related to all painful, hyperalgesic and/or inflammatory conditions in which C-fibres play a pathophysiological role by eliciting neurogenic pain or inflammation, e.g., acutely painful conditions exemplified by migraine, postoperative pain, burns, bruises, postherpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain. The present compound in the form of a modified release formulation may also be used in the treatment of conditions or indications related to urinary incontinence or angiogenesis.

Further, (R)-1-(3-(10,11-Dihydro-5H-dibenzo[a, d]cyclohepten-5-ylidene)-1-propyl)-3-piperidinecarboxylic acid or a pharmaceutically acceptable salt thereof in the form of a modified release formulation can be used in the treatment of conditions or indications caused by or related to the secretion and circulation of insulin antagonizing peptides and other peptides derived from the sensory nervous system, e.g., non-insulin-dependent diabetes mellitus (NIDDM) and ageing-associated obesity.

The above mentioned conditions or indications are herein after referred to as the disorders.

The term "treatment" as used herein includes the treatment, prevention, elimination, alleviation or amelioration of one of the above disorders.

The term "patient" as used herein includes any mammal, especially a human, in need of such treatment, prevention, elimination, alleviation or amelioration of the above disorders. Such mammals include also animals, both domestic animals, e.g. household pets, and non-domestic animals such as wildlife.

The terms "zero-order drug release" and "first-order drug release" as used herein refer to an in vitro zero-order drug release and an in vitro first-order drug release respectively.

EXAMPLES

The following examples are presented to further illustrate the present invention, but they should not be construed as limiting the invention in any manner.

Example 1

Hydroxypropylmethylcelluloses, METHOCEL K4M Premium, METHOCEL K15M Premium CR and METHOCEL K100M Premium CR, as Matrix Polymers in (R)-1-(3-(10,11-Dihydro-5H-dibenzo[a,d]cyclohepten-5-ylidene)-1-propyl)-3-piperidinecarboxylic acid, HCl tablets. Two different levels of matrix polymers have been investigated.

| | | |
|---|---|---|
| Tablet Strength, mg | 90 | 90 |
| Tablet Gross Mass, mg | 300 | 300 |
| (R)-1-(3-(10,11-Dihydro-5H-dibenzo[a,d]cyclohepten-5-ylidene)-1-propyl)-3-piperidinecarboxylic acid, hydrocloride, mg | 98.7 | 98.7 |
| Water | q.s. | q.s. |
| Matrix Polymer, mg | 60 (20%) | 180 (60%) |
| Lactose Anhydrous, mg | 136.8 | 16.8 |
| Magnesium Stearate, mg | 1.5 | 1.5 |
| Talc, mg | 3 | 3 |

(R)-1-(3-(10,11-Dihydro-5H-dibenzo[a,d]cyclohepten-5-ylidene)-1-propyl)-3-piperidinecarboxylic acid, hydroxypropylmethylcellulose, and lactose anhydrous are mixed in a high shear mixer and granulated with water. After drying, the granules are mixed with talc and magnesium stearate and compressed into tablets on a tabletting machine.

Figure 1B:
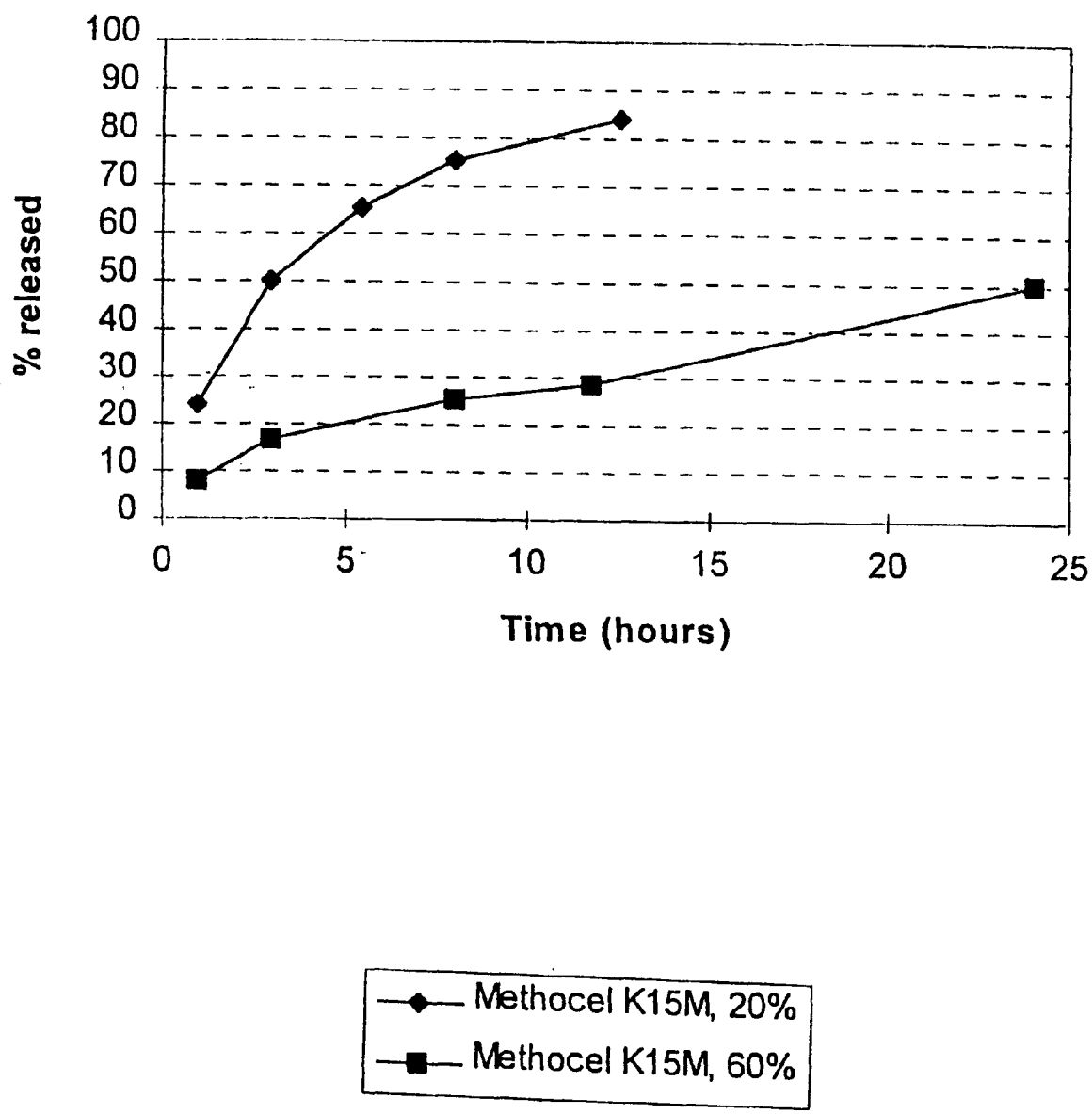
Figure 1C:
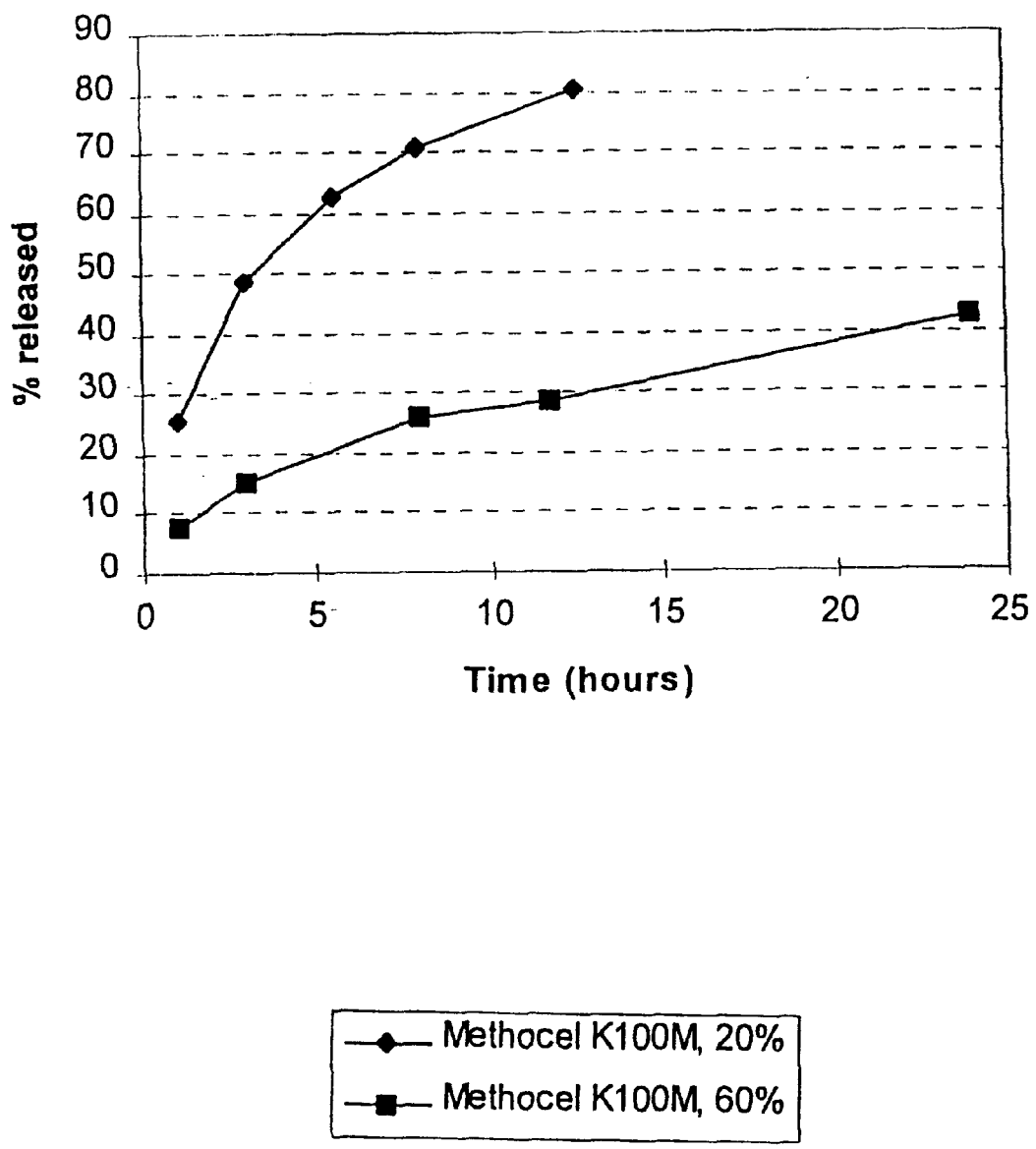

Dissolution tests have been performed according to the USP Paddle method (Water, 50 rpm, (n=3). Dissolution profiles are shown in FIGS. 1a, 1b and 1c.

Results:

When using the hydroxypropylmethylcelluloses in concentrations of 20 or 60%, first-order dissolution profiles occur.

The dissolution rates decrease as the content of matrix polymer increases.

Example 2

The high molecular weight polyethylene oxide, SENTRY POLYOX WSR 1105, as matrix polymer in (R)-1-(3-(10,11-Dihydro-5H-dibenzoa,d]cyclohepten-5-ylidene)-1-propyl)-3-piperidinecarboxylic acid tablets.

| | | |
|---|---|---|
| Tablet Strength, mg | 60 (30%) | 90 (30%) |
| Tablet Gross Mass, mg | 200 | 300 |
| (R)-1-(3-(10,11-Dihydro-5H-dibenzo[a,d]cyclohepten-5-ylidene)-1-propyl)-3-piperidinecarboxylic acid, hydrochloride, mg | 65.8 | 98.7 |
| Water | q.s. | q.s. |
| SENTRY PLOYOX WSR 1105, mg | 96 (48%) | 180 (60%) |
| Lactose anhydrous, mg | 35.2 | 16.8 |
| Magnesium Stearate, mg | 1 | 1.5 |
| Talc, mg | 2 | 3 |

(R)-1-(3-(10,11-Dihydro-5H-dibenzo[a,d]cyclohepten-5-ylidene)-1-propyl)-3-piperidinecarboxylic acid, high molecular weight polyethylene oxide, and lactose anhydrous are mixed in a high shear mixer and granulated with water. After drying, the granules are mixed with talc and magnesium stearate and compressed into tablets on a tabletting machine.

Figure 2:
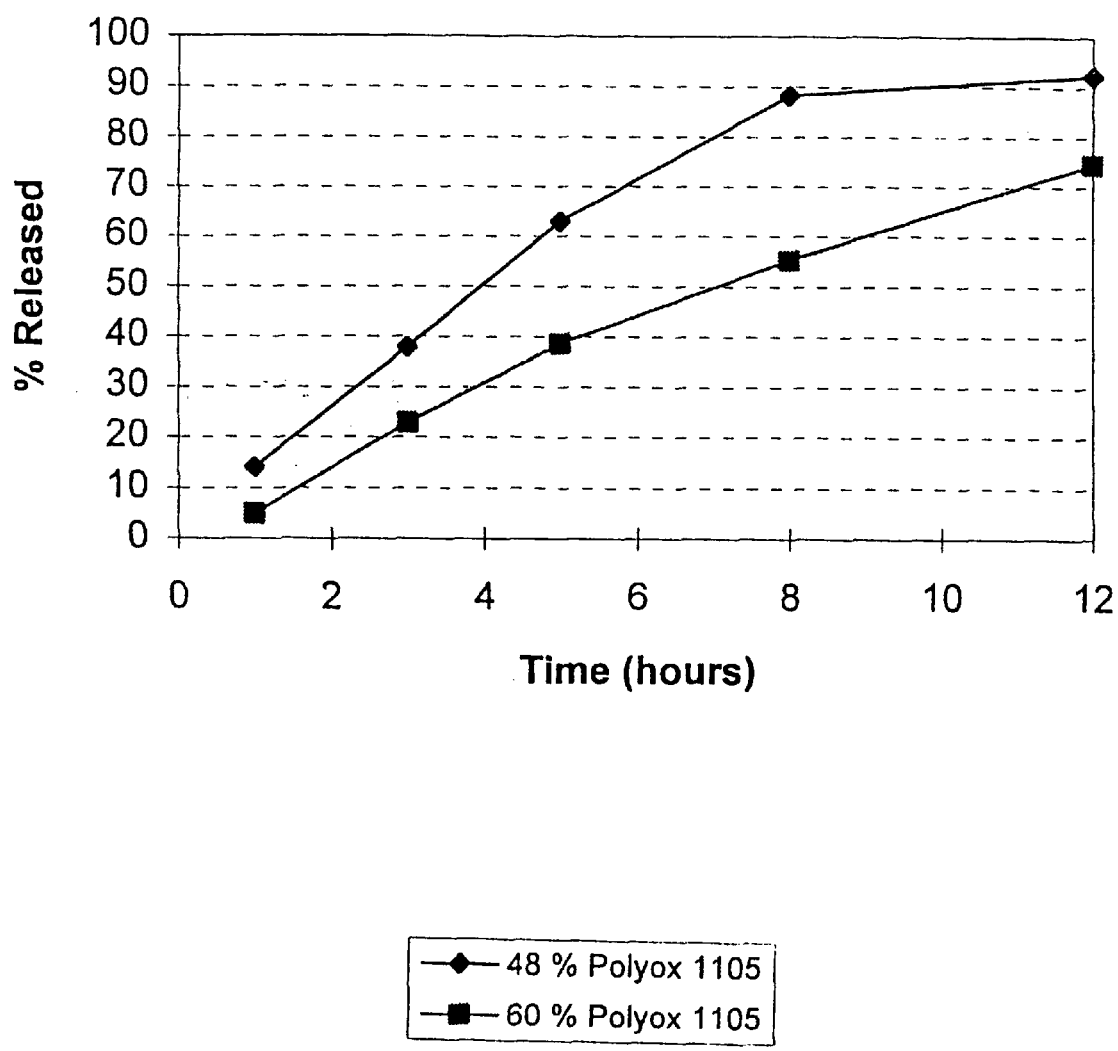
FIG. 2 is a graph depicting the in-vitro dissolution profiles for the tablet formulations shown in Example 2.

Dissolution tests have been performed according to the USP Paddle method (Water, 50 rpm, n=3). Dissolution profiles are shown in FIG. 2.

Results:

When using high molecular weight polyethylene oxide, SENTRY POLYOX WSR 1105, in concentrations of 48 or 60%, zero-order dissolution profiles occur.

The dissolution rate decreases as the content of matrix polymer increases.

Example 3

Combination of the high molecular weight polyethylene oxide, SENTRY POLYOX WSR 1105, and the hydroxypropylmethylcellulose, METHOCEL K100M Premium CR as Matrix Polymers in (R)-1-(3-(10,11-Dihydro-5H-dibenzo[a,d]cyclohepten-5-ylidene)-1-propyl)-3-piperidinecarboxylic acid Tablets.

| Tablet Strength, mg | 60 | 60 | 60 |
|---|---|---|---|
| Tablet Gross Mass, mg | 200 | 200 | 200 |
| (R)-1-(3-(10,11-Dihydro-5H-dibenzo[a,d]cyclohepten-5-ylidene)-1-propyl)-3-piperidinecarboxylic acid, hydro-chloride, mg | 65.8 | 65.8 | 65.8 |
| Water | q.s. | q.s. | q.s. |
| SENTRY POLYOX WSR 1105, mg | 96 (48%) | 72 (36%) | 48 (24%) |
| METHOCEL K100M Premium CR, mg | 24 (12%) | 48 (24%) | 72 (36%) |
| Lactose Anhydrous, mg | 11.2 | 11.2 | 11.2 |
| Magnesium Stearate, mg | 1 | 1 | 1 |
| Talc, mg | 2 | 2 | 2 |

(R)-1-(3-(10,11-Dihydro-5H-dibenzo[a,d]cyclohepten-5-ylidene)-1-propyl)-3-piperidinecarboxylic acid, high molecular weight polyethylene oxide, hydroxypropylmethyl-cellulose, and lactose anhydrous are mixed in a high shear mixer and granulated with water. After drying, the granules are mixed with talc and magnesium stearate and compressed into tablets on a tabletting machine.

Figure 3:
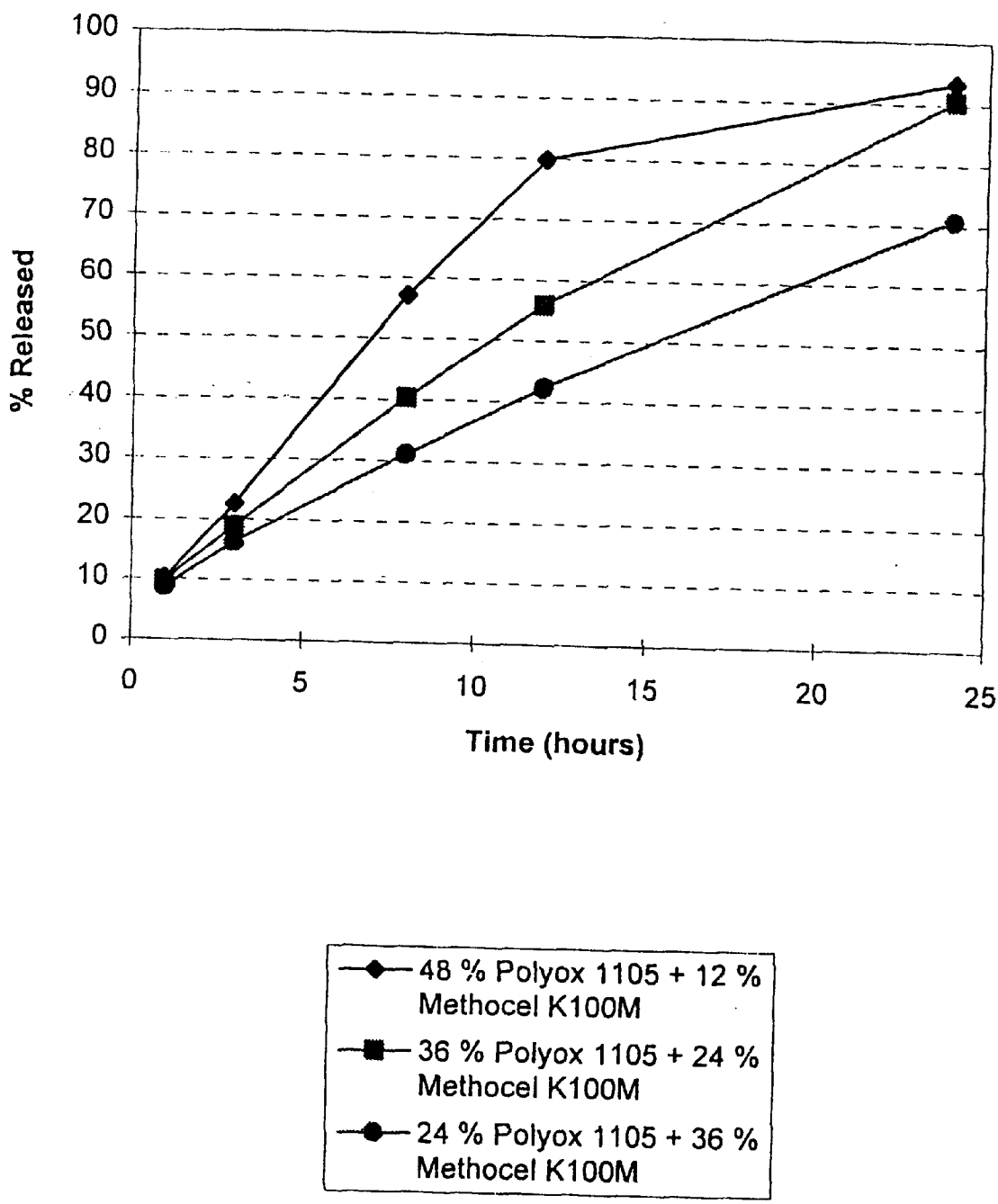
FIG. 3 is a graph depicting the in-vitro dissolution profiles for the tablet formulations shown in Example 3.

Dissolution tests have been performed according to the USP Paddle method (Water, 50 rpm, n=3). Dissolution Profiles are shown in FIG. 3.

Results:

Although hydroxypropymethylcelluloses as matrix polymers cause first-order dissolution profiles (Example 1), when combining the hydroxypropylmethylcellulose, METHOCEL KL00M Premium CR, and the high molecular weight polyethylene oxide, SENTRY POLYOX WSR 1105, zero-order dissolution profiles are obtained. Even with 24% high molecular weight polyethylene oxide and 36% hydroxypropylmethylcellulose, zero-order dissolution profiles are obtained.

It is possible to adjust the dissolution rate and dissolution profile by changing the ratio between the amounts of the two matrix polymers.

Example 4

Investigation of the dissolution profiles' pH-dependence has been performed. Two different formulations have been investigated. One formulation contains SENTRY POLYOX WSR 1105 as matrix polymer and the other contains both SENTRY POLYOX WSR 1105 and METHOCEL K100M Premium CR as matrix polymers.

| Tablet Strength, mg | 30 | 30 |
|---|---|---|
| Tablet Gross Mass, mg | 200 | 200 |
| (R)-1-(3-(10,11-Dihydro-5H-dibenzo[a,d]cyclohepten-5-ylidene)-1-propyl)-3-piperidinecarboxylic acid, hydrochloride, mg | 32.9 | 32.9 |
| Water | q.s. | q.s. |
| SENTRY POLYOX WSR 1105, mg | 96 (48%) | 72 (36%) |
| METHOCEL K100M Premium CR, mg | 0 | 48 (24%) |
| Lactose Anhydrous, mg | 68.1 | 11.2 |
| Magnesium Stearate, mg | 1 | 1 |
| Talc, mg | 2 | 2 |

(R)-1(10,11-Dihydro-5H-dibenzo[a,d]cyclohepten-5-ylidene)-1-propyl)-3-piperidinecarboxylic acid, martrix polymer(s), and lactose anhydrous are mixed in a high shear mixer and granulated with water. After drying, the granules are mixed with talc and magnesium stearate and compressed into tablets on a tabletting machine.

Dissolution tests have been performed according to the USP Paddle method (50 rpm, n=3) in the following media:

Water
0.1 N hydrochloric acid (pH 1)
0.07 M phosphate buffer (pH 4.75)
Phosphate-citrate buffer (pH 6.8)

Figure 4A:
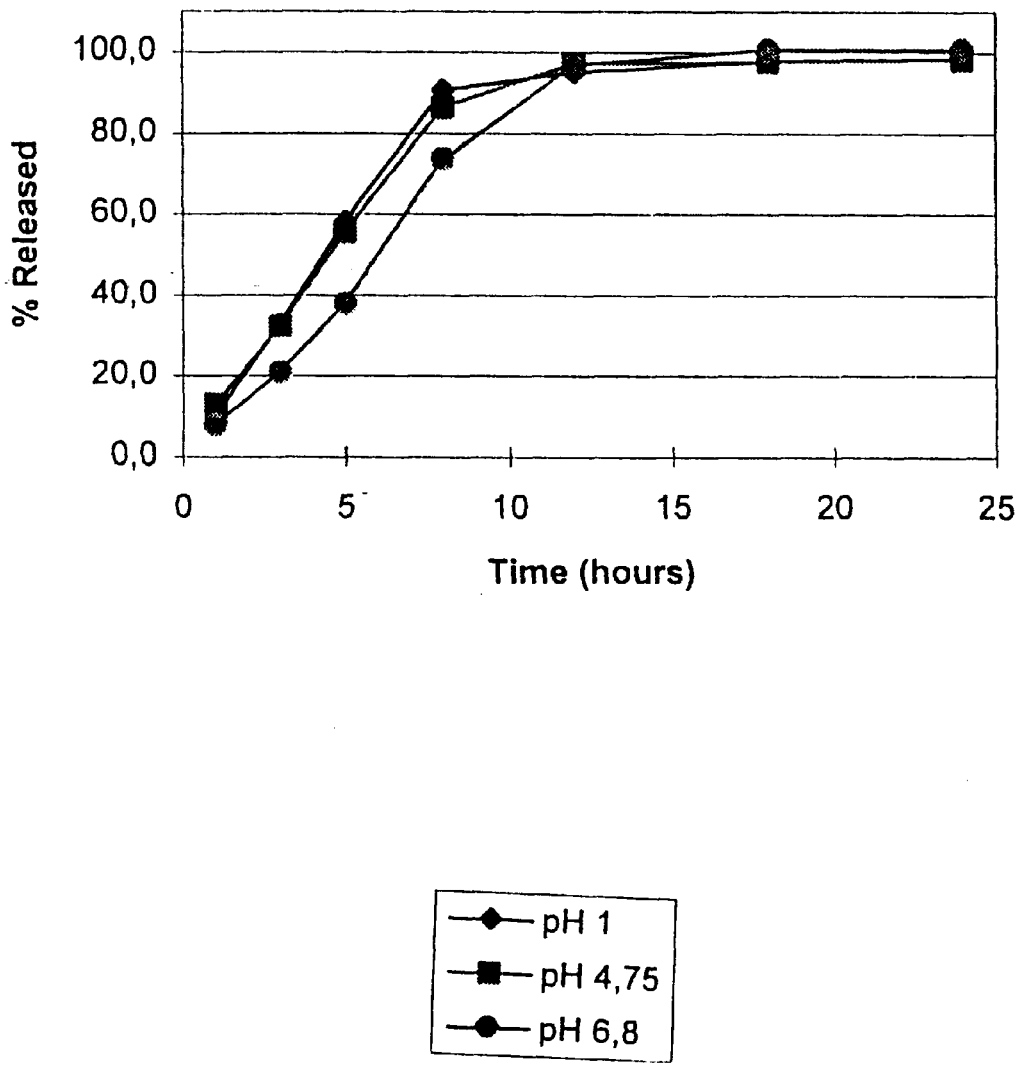
FIGS. 4a and 4b are graphs depicting in-vitro dissolution profiles for the tablet formulations shown in Example 4.

Dissolution Profiles for the tablets with SENTRY POLYOX WSR 1105 are shown in FIG. 4a.

Figure 4B:
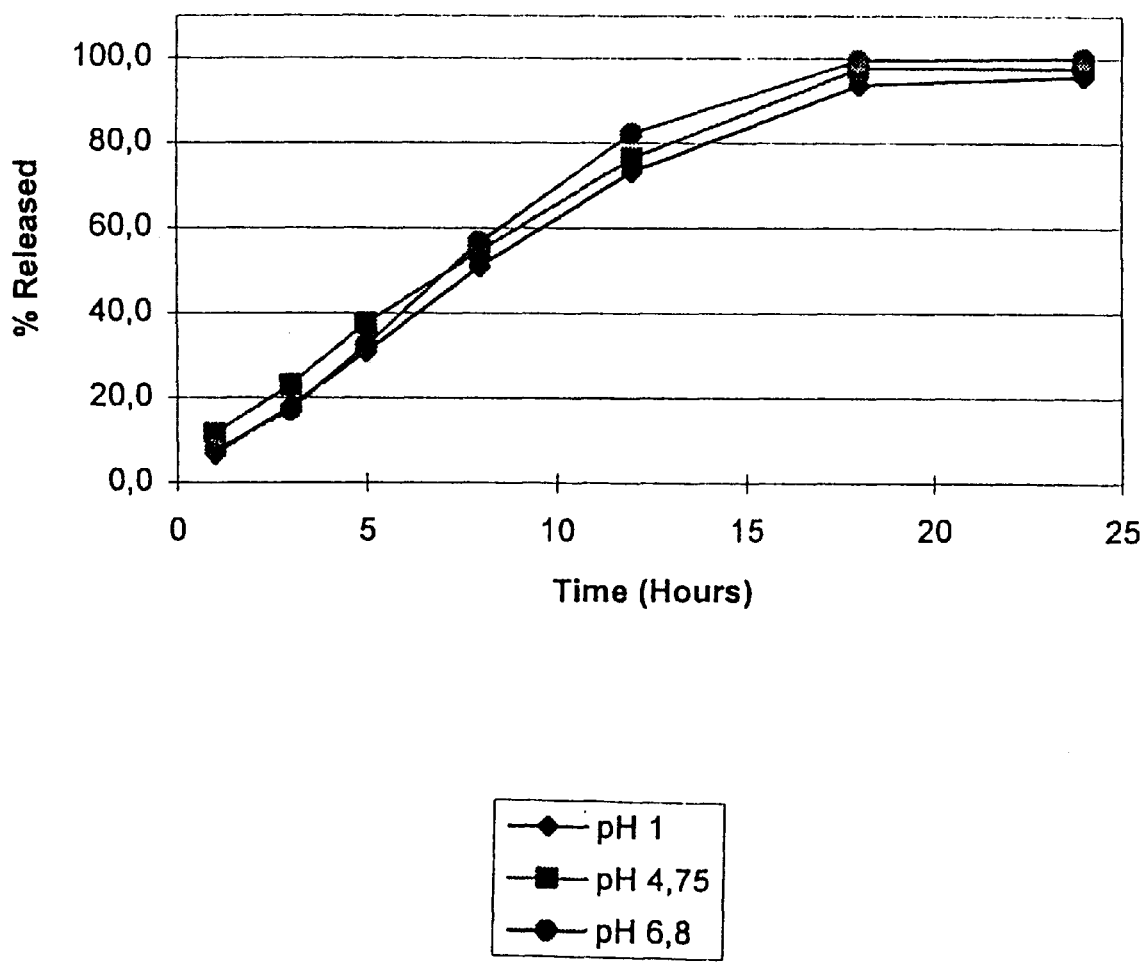

Dissolution Profiles for the tablets with SENTRY POLYOX WSR 1105 and METHOCEL K100 Premium CR are shown in FIG. 4b.

pH Dissolution Profiles

Results

By combining hydroxymethylpropylcellulose, METHOCEL K100M Premium CR and the high molecular weight polyethylene oxide, SENTRY POLYOX WSR 1105, zero-order release is obtained independent of pH in the dissolution media.

What is claimed is:

1. A modified release formulation, comprising: (R)-1-(3-(10,11-Dihydro-5H-dibenzo[a,d]cyclohepten-5-ylidene)-1-propyl)-3-piperidinecarboxylic acid or a pharmaceutically acceptable salt thereof dispersed in a polymeric matrix containing at least one release rate controlling polymer, wherein the formulation exhibits a zero-order release rate.

2. The formulation of claim 1, wherein the at least one release rate controlling polymer is selected from the group consisting of hydroxypropylmethylcellulose, polyethylene oxide, and mixtures thereof.

3. The formulation of claim 1, wherein the at least one release rate controlling polymer is selected from the group consisting of hydroxypropylmethylcellulose having a viscosity of about 100 to 100,000 cps, polyethylene oxide having a molecular weight of about 100,000 to 7,000,000, and mixtures thereof.

4. The formulation of claim 1, wherein the at least one release rate controlling polymer comprises from about 5 to 75% by weight of the formulation.

5. The formulation of claim 4, wherein the at least one release rate controlling polymer comprises from about 20 to 50% by weight of the formulation.

6. The formulation of claim 1, wherein (R)-1-(3-(10,11-Dihydro-5H-dibenzo[a,d]cyclohepten-5-ylidene)-1-propyl)-3-piperidinecarboxylic acid is in the form of the hydrochloride salt.

7. The formulation of claim 1 in the form of enteric coated tablets or capsules, wax or polymer coated tablets or capsules or time-release matrices, or combinations thereof.

8. The formulation of claim 7, wherein the formulation is in the form of matrix tablets.

9. A method of treating disorders related to neurogenic inflammation comprising administering an effective amount of a formulation of claim 1 to a patient in need thereof.

10. A method of treating disorders related to non-insulin-dependent diabetes mellitus (NIDDM) comprising administering an effective amount of a formulation of claim 1 to a patient in need thereof.

* * * * *

UNITED STATES PATENT AND TRADEMARK OFFICE
CERTIFICATE OF CORRECTION

PATENT NO. : 6,207,682 B1
DATED : March 27, 2001
INVENTOR(S) : Andersen et al.

It is certified that error appears in the above-identified patent and that said Letters Patent is hereby corrected as shown below:

<u>Title page, Item [54],</u>
TITLE OF THE INVENTION:

Please delete "Modified Release Formulations Containing (R)-1-(10,11-Dihydro-5H-dibenzo[a,d]cyclohepten-5-ylidene)-1 propyl)-3-piperidinecarboxylic acid"
and insert -- Modified Release Formulations Containing (R) -1-3-(10,11-Dihydro-5H-dibenzo[a,d]cyclohepten-5-ylidene)-1-propyl)3-piperidinecarboxylic acid --

Signed and Sealed this

Sixteenth Day of October, 2001

Attest:

NICHOLAS P. GODICI
Attesting Officer
Acting Director of the United States Patent and Trademark Office